US010337069B2

(12) United States Patent
Courtney et al.

(10) Patent No.: US 10,337,069 B2
(45) Date of Patent: Jul. 2, 2019

(54) METHOD FOR DIAGNOSING HEPATIC FIBROSIS

(71) Applicants: VAIOMER, Labege (FR); Università degli Studi di Roma Tor Vergata, Rome (IT); FUNDACIÓ INSTITUT D'INVESTIGACIÓ BIOMÈDICA DE GIRONA DR. JOSEP TRUETA, Girona (ES)

(72) Inventors: Michael Courtney, Lyons (FR); Benjamin Lelouvier, Toulouse (FR); Massimo Federici, Rome (IT); Jose Manuel Fernandez-Real, Gerone (ES); Sandrine Païssé, Toulouse (FR)

(73) Assignees: VAIOMER, Labege (FR); UNIVERSITÀ DEGLI STUDI DI ROMA TOR VERGATA, Rome (IT); FUNDACIÓ INSTITUT D'INVESTIGACIÓ BIOMÈDICA DE GIRONA DR. JOSEP TRUETA, Girona (IT)

( * ) Notice: Subject to any disclaimer, the term of this patent is extended or adjusted under 35 U.S.C. 154(b) by 0 days.

(21) Appl. No.: 15/305,598

(22) PCT Filed: Apr. 23, 2015

(86) PCT No.: PCT/EP2015/058772
§ 371 (c)(1),
(2) Date: Oct. 20, 2016

(87) PCT Pub. No.: WO2015/162200
PCT Pub. Date: Oct. 29, 2015

(65) Prior Publication Data
US 2017/0044612 A1    Feb. 16, 2017

(30) Foreign Application Priority Data

Apr. 23, 2014  (EP) .................................. 14305597

(51) Int. Cl.
*C12Q 1/68* (2018.01)
*C12Q 1/6883* (2018.01)
*C12Q 1/689* (2018.01)

(52) U.S. Cl.
CPC .......... *C12Q 1/6883* (2013.01); *C12Q 1/689* (2013.01); *C12Q 2600/112* (2013.01); *C12Q 2600/136* (2013.01)

(58) Field of Classification Search
None
See application file for complete search history.

(56) References Cited

U.S. PATENT DOCUMENTS

| 2009/0304704 A1 | 12/2009 | Gerhard et al. |
| 2012/0021421 A1* | 1/2012 | Amar ................ C12Q 1/6883 435/6.12 |
| 2014/0088203 A1 | 3/2014 | Amar et al. |
| 2014/0186829 A1 | 7/2014 | Burcelin et al. |

OTHER PUBLICATIONS

Amar et al. EMBO (2011 EMBO Mol Med 3, 559-572) (Year: 2011).*
Gabele et al. (Journal of Hepatology 2011 vol. 55 1391-1399) (Year: 2011).*
Campos et al. (Hepatology 2008;47:1916-1923) (Year: 2008).*
International Search Report for PCT/EP2015/058772, dated Jun. 11, 2015.
Written Opinion for PCT/EP2015/058772, completed May 27, 2015.
Dae Won Jun et al: "Association Between Small Intestinal Bacterial Overgrowth and Peripheral Bacterial DNA in Cirrhotic Patients", Digestive Diseases and Sciences, Kluwer Academic Publishers-Plenum Publishers, NE, vol. 55, No. 5, Jun. 11, 2009(Jun. 11, 2009), pp. 1465-1471, XP019816559, ISSN: 1573-2568 the whole document.
J. K. Dyson et al: "Non-alcoholic fatty liver disease: a practical approach to diagnosis and staging", Frontline Gastroenterology, vol. 5, No. 3, Dec. 24, 2013(Dec. 24, 2013), pp. 211-218, XP055143272, DOI: 10.1136/flgastro-2013-100403 abstract; table 4.
Jean-Marc Sabate et al: "High Prevalence of Small Intestinal Bacterial Overgrowth in Patients with Morbid Obesity: A Contributor to Severe Hepatic Steatosis", Obesity Surgery, vol. 18, No. 4, Feb. 20, 2008 (Feb. 20, 2008), pp. 371-377, XP055143104, ISSN: 0960-8923, DOI: 10.1007/s11695-007-9398-2 the whole document.
Aron-Wisnewsky J et al: "Gut microbiota and non-alcoholic fatty liver disease: new insights.", Clinical Microbiology and Infection : The Official Publication of the European Society of Clinical Microbiology and Infectious Diseases Apr. 2013, vol. 19, No. 4, Apr. 2013(Apr. 2013), pp. 338-348, XP002740162, ISSN: 1469-0691.
E. Seki et al: "Role of innate immunity and the microbiota in liver fibrosis: crosstalk between the liver and gut", The Journal of Physiology, vol. 590, No. 3, Nov. 28, 2011(Nov. 28, 2011), pp. 447-458, XP055142520, ISSN: 0022-3751, DOI: 10.1113/jphysiol. 2011.219691 abstract; figure 3 p. 454, col. 2-p. 455, col. 1.

* cited by examiner

*Primary Examiner* — Juliet C Switzer
(74) *Attorney, Agent, or Firm* — B. Aaron Schulman, Esq.; Stites & Harbison, PLLC

(57) ABSTRACT

The present invention concerns methods, in particular in vitro methods, for diagnosing liver fibrosis in a subject suffering from obesity, or for selecting a subject suffering from obesity for liver biopsy or for treatment. The present invention also pertains to methods for screening a probiotic, a prebiotic, a chemical compound or a biological compound suitable for preventing and/or treating liver fibrosis.

11 Claims, 2 Drawing Sheets
Specification includes a Sequence Listing.

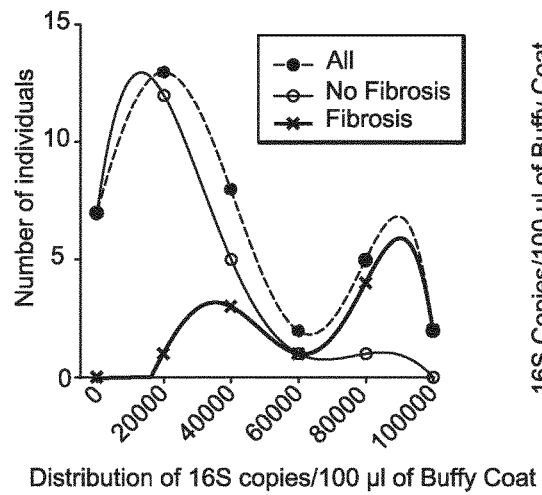
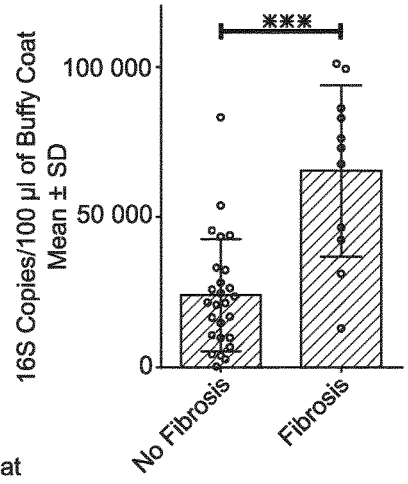
FIG.1    FIG.2
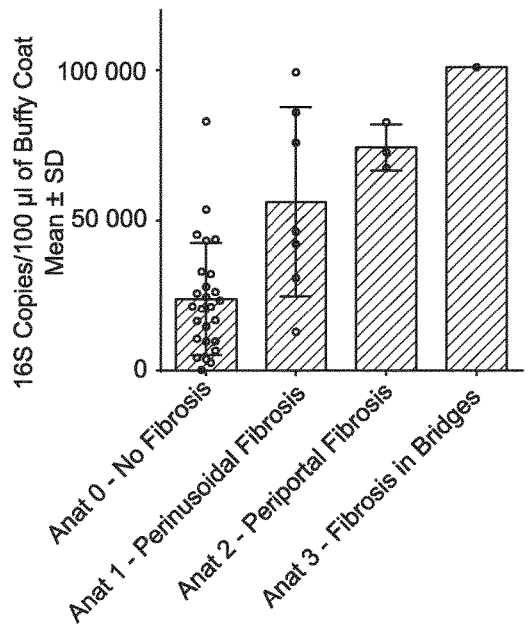
FIG.3

SEQUENCE LISTING

```
<160> NUMBER OF SEQ ID NOS: 3

<210> SEQ ID NO 1
<211> LENGTH: 1542
<212> TYPE: DNA
<213> ORGANISM: Escherichia coli

<400> SEQUENCE: 1
aaattgaaga gtttgatcat ggctcagatt gaacgctggc ggcaggccta acacatgcaa      60
gtcgaacggt aacaggaagc agcttgctgc tttgctgacg agtggcggac gggtgagtaa     120
tgtctgggaa actgcccgat ggagggggat aactactgga aacggtagct aataccgcat     180
aacgtcgcaa gaccaaagag ggggaccttc gggcctcttg ccatcggatg tgcccagatg     240
ggattagcta gtaggtgggg taacggctca cctaggcgac gatccctagc tggtctgaga     300
ggatgaccag ccacactgga actgagacac ggtccagact cctacgggag gcagcagtgg     360
ggaatattgc acaatgggcg caagcctgat gcagccatgc cgcgtgtatg aagaaggcct     420
tcgggttgta aagtactttc agcggggagg aagggagtaa agttaatacc tttgctcatt     480
gacgttaccc gcagaagaag caccggctaa ctccgtgcca gcagccgcgg taatacggag     540
ggtgcaagcg ttaatcggaa ttactgggcg taaagcgcac gcaggcggtt tgttaagtca     600
gatgtgaaat ccccgggctc aacctgggaa ctgcatctga tactggcaag cttgagtctc     660
gtagaggggg gtagaattcc aggtgtagcg gtgaaatgcg tagagatctg gaggaatacc     720
ggtggcgaag gcggcccct ggacgaagac tgacgctcag gtgcgaaagc gtgggagca     780 aacaggatta gataccctgg tagtccacgc cgtaaacgat gtcgacttgg aggttgtgcc     840
cttgaggcgt ggcttccgga gctaacgcgt taagtcgacc gcctggggag tacggccgca     900
aggttaaaac tcaaatgaat tgacggggc ccgcacaagc ggtggagcat gtggtttaat     960
tcgatgcaac gcgaagaacc ttacctggtc ttgacatcca cggaagtttt cagagatgag    1020
aatgtgcctt cgggagccgt gagacaggtg ctgcatggct gtcgtcagct cgtgttgtga    1080
aatgttgggt taagtcccgc aacgagcgca acccttatcc tttgttgcca gcggtccggc    1140
cgggaactca aaggagactg ccagtgataa actggaggaa ggtggggatg acgtcaagtc    1200
```

```
atcatggccc ttacgaccag ggctacacac gtgctacaat ggcgcataca aagagaagcg    1260
acctcgcgag agcaagcgga cctcataaag tgcgtcgtag tccggattgg agtctgcaac    1320
tcgactccat gaagtcggaa tcgctagtaa tcgtggatca gaatgccacg gtgaatacgt    1380
tcccgggcct tgtacacacc gcccgtcaca ccatgggagt gggttgcaaa agaagtaggt    1440
agcttaacct tcgggagggc gcttaccact ttgtgattca tgactggggt gaagtcgtaa    1500
caaggtaacc gtaggggaac ctgcggttgg atcacctcct ta                      1542

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
tcctacggga ggcagcagt                                                  19

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
ggactaccag ggtatctaat cctgtt                                          26
```

METHOD FOR DIAGNOSING HEPATIC FIBROSIS

The present invention concerns methods for diagnosing liver fibrosis in a subject suffering from obesity, or for selecting a subject suffering from obesity for liver biopsy or for treatment. The present invention also pertains to methods for screening a probiotic, a prebiotic, a chemical compound or a biological compound suitable for preventing and/or treating liver fibrosis.

The liver is the first extra-intestinal organ that encounters venous blood from the small and large intestines via the portal vein. In a healthy organism only minor quantities of translocated bacterial products reach the liver. In general, the hepatic immune system tolerates these bacterial products, avoiding harmful responses, a phenomenon known as 'liver tolerance'. In this respect, the liver not only consists of parenchymal hepatocytes, but also contains non-parenchymal cells including immune and non-immune cells. Members of the hepatic immune system are resident liver tissue macrophages (Kupffer cells), natural killer (NK) cells, NKT cells, T cells and B cells. These cell types strictly regulate the liver immune system including liver tolerance.

Several lines of evidence suggest that bacterial translocation plays a significant role in alcoholic liver diseases. It has been observed that impairment of the function of intestinal tight junctions and bacterial proliferation in the gut induced by alcohol and/or its metabolites, such as acetaldehyde, enhance bacterial translocation to the liver. This in turn leads to activation of immune cells, including Kupffer cells, and the release of various pro-inflammatory cytokines and chemokines. In addition, it has been observed that there is reduced intestinal expression of the antimicrobial proteins Reg3b and Reg3g in animals and patients with chronic ethanol consumption, which suggests that ethanol-induced gut dysbiosis is mediated by the deregulation of the expression of antimicrobial molecules.

In non-alcoholic steatohepatitis (NASH), evidence of the role of bacterial translocation into the liver also exists. Firstly, the role of gut flora in obesity has been demonstrated. When wild-type germ-free mice fed a standard chow diet were colonized with a microbiota harvested from ob/ob or lean donors, adiposity in recipients of the "obese" microbiota increased more than in recipients of a "lean" microbiota, indicating a crucial role of the microbiota in obesity and hence fatty liver disease. However, to the inventors' knowledge, no correlation has ever been established between bacterial translocation into the liver, or even into the blood circulation, of a subject and the presence of liver fibrosis in said subject.

Liver fibrosis is a significant health problem with a worldwide mortality attributable to cirrhosis and primary liver cancer of around 1.5 million deaths per year. Cirrhosis is the last stage of fibrosis which occurs mainly in response to viral and toxic-metabolic insults. The most common causes of fibrosis progression are chronic hepatitis C, chronic hepatitis B, alcoholic liver disease and non-alcoholic fatty liver disease. Liver fibrosis is treatable, even at the cirrhotic stage, mainly using anti-viral treatments for hepatitis C and B, but also by reducing alcohol consumption and improving overweight, diabetes and metabolic factors for non-alcoholic fatty liver disease.

Therefore, screening for liver fibrosis is desirable. Liver biopsy is the standard for diagnosing hepatic fibrosis and for diagnosing the underlying liver disorder causing fibrosis. However, liver biopsy is invasive, resulting in a 10 to 20% risk of minor complications (e.g. postprocedural pain) and a 0.5 to 1% risk of serious complications (e.g. significant bleeding). Also, liver biopsy is limited by sampling error and imperfect inter-observer agreement in interpretation of histologic findings. Thus, liver biopsy may not always be done, and alternative non-invasive methods for diagnosing liver fibrosis are highly needed.

The present invention first arises from the unexpected finding by the inventors that the blood concentration of bacterial 16S rDNA is specifically correlated to the presence of liver fibrosis in patients suffering from obesity, whereas it is not correlated to other kind of fatty liver diseases, such as e.g. liver steatosis. The blood concentration of bacterial 16S rDNA may thus be useful in the diagnosis of liver fibrosis in patients suffering from obesity.

The present invention thus relates to a method, in particular an in vitro method, for diagnosing liver fibrosis in a subject suffering from obesity, said method comprising the steps of:

a1) measuring the concentration of bacterial 16S rDNA, or the ratio of the quantity of bacterial 16S rDNA to the quantity of total DNA, in a biological sample of the subject; and b) based on the result of the measurement in step a1), diagnosing liver fibrosis in the subject suffering from obesity.

The present invention also concerns a method, in particular an in vitro method, for selecting a subject suffering from obesity for liver biopsy, said method comprising the steps of:

a1) measuring the concentration of bacterial 16S rDNA, or the ratio of the quantity of bacterial 16S rDNA to the quantity of total DNA, in a biological sample of the subject; and b) based on the result of the measurement in step a1), selecting the subject suffering from obesity to undergo liver biopsy.

According to another aspect, the invention relates to an in vitro method for selecting a subject suffering from obesity for treatment regimen targeting liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject; and b) based on the result of the measurement in step a1), selecting the subject suffering from obesity to undergo treatment regimen targeting liver fibrosis and/or its complications.

Another aspect of the present invention is a method for treating an obese subject suffering from liver fibrosis, said method comprising the steps of:

a1) measuring the concentration of bacterial 16S rDNA, or the ratio of the quantity of bacterial 16S rDNA to the quantity of total DNA, in a biological sample of the subject;

b) based on the result of the measurement in step a1), diagnosing liver fibrosis in the subject suffering from obesity; and c) administering to the subject a treatment targeting liver fibrosis, if liver fibrosis has been diagnosed in step b).

The invention further pertains to a method for treating a subject suffering from obesity and from liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject;

b) based on the result of the measurement in step a1), selecting the subject suffering from obesity to undergo drug treatment targeting liver fibrosis and/or its complications; and c) administering to the subject selected in step b) a drug treatment targeting liver fibrosis and/or its complications.

The invention also relates to in vitro method for monitoring the responsiveness of a patient suffering from obesity and from liver fibrosis and/or its complications to a drug treatment targeting liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject; and b) based on the result of the measurement in step a1), monitoring the responsiveness of the patient to said drug treatment.

The blood concentration of bacterial 16S rDNA reflects the cause of the disease rather than its consequence, and may therefore be useful as a companion biomarker to therapeutic strategies targeting gut microbiota, such as pre and probiotics.

Accordingly, the present invention finally pertains to a method for screening a probiotic, a prebiotic, a chemical compound or a biological compound suitable for preventing and/or treating liver fibrosis, comprising the steps of:

measuring the concentration of bacterial 16S rDNA, or the ratio of the quantity of bacterial 16S rDNA to the quantity of total DNA, in a biological sample of an obese subject suffering from liver fibrosis who has been treated with the candidate probiotic, prebiotic, chemical compound or biological compound; and comparing said concentration, or said ratio, with that of a control obese subject suffering from liver fibrosis who has not been treated with said candidate probiotic, prebiotic, chemical compound or biological compound;

wherein a higher concentration, or a higher ratio, measured in the biological sample of the control subject than in the biological sample of the subject treated with the candidate probiotic, prebiotic, chemical compound or biological compound, indicates that said candidate probiotic, prebiotic, chemical compound or biological compound is suitable for preventing and/or treating liver fibrosis.

DETAILED DESCRIPTION OF THE INVENTION

Fibrosis

As used herein, the terms "fibrosis", "liver fibrosis" or "hepatic fibrosis" refer to a medical condition in which excessive connective tissue accumulates in the liver; this tissue represents scarring in response to chronic, repeated liver cell injury. Commonly, fibrosis progresses, disrupting hepatic architecture and eventually function, as regenerating hepatocytes attempt to replace and repair damaged tissue.

Subject

In the context of the present invention, a "subject" denotes a human or non-human mammal, such as a rodent (rat, mouse, rabbit), a primate (chimpanzee), a feline (cat), or a canine (dog). Preferably, the subject is human. The subject according to the invention may be in particular a male or a female.

According to the present invention, the subject suffers from obesity.

As used herein, the term "obesity", "general obesity" or "overall obesity" refers to a medical condition in which excess body fat has accumulated to the extent that it may have an adverse effect on health, leading to reduced life expectancy and/or increased health problems. General obesity is typically determined by assessing the body mass index (BMI), a measurement which associates weight and height. In particular, people are defined as overweight if their BMI is between 25 $kg/m^2$ and 30 $kg/m^2$, and obese when it is greater than 30 $kg/m^2$.

In the context of the invention, the subject has preferably a body mass index (BMI) higher than 30 $kg/m^2$, more preferably than 37.5 $kg/m^2$, or even more preferably higher than 40 $kg/m^2$.

In the context of the invention, the term "abdominal obesity", "central obesity" or "belly fat" refers to obesity wherein there is a specific accumulation of abdominal fat resulting in an increase in waist size. Typically, in abdominal obesity, visceral fat, also known as organ fat or intra-abdominal fat, is located inside the peritoneal cavity, packed in between internal organs and torso, whereas, in general obesity, subcutaneous fat is found underneath the skin, and intramuscular fat is found interspersed in skeletal muscle.

Abdominal obesity is typically determined just by looking at the naked body, or more specifically by taking waist and hip measurements. The absolute waist circumference (>102 centimeters (40 inches) in men and >88 centimeters (35 inches) in women) and the waist-hip ratio (>0.9 for men and >0.85 for women) are both used as measures of abdominal obesity. Preferably, the expression "abdominal adiposity" according to the invention refers to a waist circumference of more than 102 cm in men or of more than 88 cm in women.

Preferably, the subject according to the invention suffers from non-alcoholic fatty liver disease (NAFL disease) at the time of sampling. More preferably, the subject according to the invention suffers from non-alcoholic steatohepatitis (NASH) at the time of sampling.

"Non-alcoholic fatty liver disease" or "NAFL disease" is a term used herein to describe the accumulation of fat in the liver of people who drink little or no alcohol. In many cases, NAFL disease is linked to obesity. NAFL disease is common and, for most people, causes no signs and symptoms and no complications. But in some people with NAFL disease, the fat that accumulates can cause inflammation and scarring in the liver. This more serious form of NAFL disease is called non-alcoholic steatohepatitis (NASH).

In the context of the invention, the expression "non-alcoholic steatohepatitis" or "NASH" refers to a disease characterized by fat accumulation (steatosis) and inflammation. Steatosis results from hepatic triglyceride accumulation. NASH can cause damage in the liver resulting in fibrosis.

In a particular embodiment, the subject has a body mass index (BMI) higher than 37.5 $kg/m^2$ and suffers from at least two metabolic co-morbidities selected from the group consisting of type 2 diabetes, hypertension and dyslipidemia.

As used herein, "diabetes" or "diabetes mellitus" denotes a metabolic disorder in which the pancreas produces insufficient amounts of insulin, or in which the cells of the body fail to respond appropriately to insulin thus preventing cells from absorbing glucose. As a result, glucose builds up in the blood. This high blood glucose level produces the classical symptoms of polyuria (frequent urination), polydipsia (increased thirst) and polyphagia (increased hunger). The term "diabetes" includes type 1 diabetes, type 2 diabetes, gestational diabetes (during pregnancy) and other states that cause hyperglycemia.

Type 2 diabetes, also known as non-insulin-dependent diabetes mellitus (NIDDM) and adult-onset diabetes, is associated with predominant insulin resistance and thus relative insulin deficiency and/or a predominantly insulin secretory defect (or insulinopenia) with insulin resistance. More specifically, type 2 diabetes may be associated either with (i) a predominant insulin resistance with a moderate insulinopenia or with (ii) a moderate insulin resistance with a predominant insulinopenia.

As used herein, the term "hypertension" also referred to as "high blood pressure", "HTN" or "HPN", denotes a medical condition in which the blood pressure is chronically elevated. In the context of the invention, hypertension is preferably defined by systolic/diastolic blood pressure of at least 140/90 mmHg or being on antihypertensive medication.

As used herein, the term "dyslipidemia" denotes an elevation of plasma cholesterol, triglycerides or both, or a low high-density lipoprotein level that may contribute to the development of atherosclerosis.

In a particular embodiment, the subject is free of known systemic disease such as rheumatoid arthritis, hypertension or systemic lupus erythematosus, serious chronic illness such as cardiovascular disease or cancer, and/or ethanol intake superior to 20 grammes per day.

In another particular embodiment, the subject according to the invention did not display infection symptom(s) during the month preceding sampling. Accordingly, the subject according to the invention preferably displays a plasma baseline C reactive protein concentration lower than 10 mg/l and/or does not present an abundant leukocyturia and/or does not take antiviral therapy.

As used herein, the term "C reactive protein" or "CRP" refers to a protein which is a member of the class of acute-phase reactants, as its levels rise dramatically during inflammatory processes occurring in the body. As known from the skilled person, CRP is typically a 224-residue protein with a monomer molar mass of 25 kDa, encoded by the CRP gene.

As used herein, the term "leukocyturia" refers to the presence of leukocytes in the urine of the subject. In particular, an abundant leukocyturia corresponds typically to the presence of more than 10 leukocytes/mm$^3$ in the urine.

Bacterial 16S rDNA

In the context of the invention, the expressions "16S rDNA" and "16S ribosomal DNA" are used indifferently and refer to the gene encoding the 16S ribosomal RNA constituted of about 1500 nucleotides, which is the main component of the small prokaryotic ribosomal subunit (30S). 16S rDNA is highly conserved among bacteria. The reference *Escherichia coli* 16S rDNA gene sequence corresponds to SEQ ID NO: 1 (called rrs). In the context of the invention, 16S rDNA refers to any sequence corresponding to SEQ ID NO: 1 in other bacterial strains.

Biological Sample

As used herein, the term "biological sample" means a substance of biological origin. Examples of biological samples include blood and components thereof such as serum, plasma, platelets, buffy coat (leucocytes), erythrocytes, urine, saliva, fecal water and tissues such as adipose tissues, hepatic tissues, pancreatic tissues and the like. Preferably, a biological sample according to the present invention is a blood, serum, plasma, buffy coat, urine, adipose tissue or hepatic tissue sample. More preferably, the biological sample is selected from the group consisting of blood, buffy coat, serum and plasma sample. The biological sample according to the invention may be obtained from the subject by any appropriate means of sampling known from the skilled person.

In Vitro Method for Diagnosing Liver Fibrosis

The present invention concerns an in vitro method for diagnosing liver fibrosis in a subject suffering from obesity, said method comprising the steps of:
a1) measuring the concentration of bacterial 16S rDNA, or the ratio of the quantity of bacterial 16S rDNA to the quantity of total DNA, in a biological sample of the subject; and
b) based on the result of the measurement in step a1), diagnosing liver fibrosis in the subject suffering from obesity.

Liver biopsy is the standard for diagnosing liver fibrosis and for diagnosing the underlying liver disorder causing fibrosis. However, liver biopsy is invasive. Therefore, liver biopsy should not be done systematically, but rather to confirm the presence of liver fibrosis in a subject.

Thus the present invention also concerns an in vitro method for selecting a subject suffering from obesity for liver biopsy, said method comprising the steps of:
a1) measuring the concentration of bacterial 16S rDNA, or the ratio of the quantity of bacterial 16S rDNA to the quantity of total DNA, in a biological sample of the subject; and
b) based on the result of the measurement in step a1), selecting the subject suffering from obesity to undergo liver biopsy.

Preferably, the concentration of bacterial 16S rDNA, or the ratio of the quantity of bacterial 16S rDNA to the quantity of total DNA (noted "16S rDNA/total DNA ratio"), is measured by polymerase chain reaction (PCR), more preferably by quantitative PCR (qPCR), most preferably by real-time or real-time quantitative PCR (RT-PCR or RT-qPCR).

As used herein, "real-time PCR", "real-time quantitative PCR", "real-time polymerase chain reaction" or "kinetic polymerase chain reaction" refers to a laboratory technique based on the polymerase chain reaction, which is used to amplify and simultaneously quantify a targeted DNA molecule. It enables both detection and quantification (as absolute number of copies or relative amount when normalized to DNA input or additional normalizing genes) of a specific sequence in a sample. Two common methods of quantification are the use of fluorescent dyes that intercalate with double-stranded DNA, and modified DNA oligonucleotide probes that emit fluorescence when hybridized with a complementary DNA.

In the context of the invention, the real-time PCR is preferably performed using the universal forward and reverse primers eubac-F (5'-TCCTACGGGAGGCAGCAGT-3' SEQ ID NO: 2) and eubac-R (5'-GGACTACCAGGGTATCTAATCCTGTT-3' SEQ ID NO: 3). Typically, the amplification is performed using 2 μl of DNA in a total reaction volume of 12.5 μl, using for instance Sybr Green RT-qPCR technologies, typically with the following cycle: hold stage of 10 min at 95° C., then 40 cycles of 15 sec at 95° C., 1 min at 63° C. and 1 min at 72° C. Typically, specificity of the qPCR reaction is assessed by analysis of a post-PCR melting curve for example between 60° C. and 95° C.

Specifically, the inventors demonstrated that the concentration of bacterial 16S rDNA (for instance the number of copies per ml of blood), or the 16S rDNA/total DNA ratio (for instance the number of copies per µg of total DNA), is significantly higher in biological samples of subjects with liver fibrosis.

The 16S rDNA concentration is preferably measured by real-time PCR, preferably using the universal forward and reverse primers eubac-F (5'-TCCTACGGGAGGCAGCAGT-3' SEQ ID NO: 2) and eubac-R (5'-GGACTACCAGGGTATCTAATCCTGTT-3' SEQ ID NO: 3). Typically, the amplification is performed using 2 µl of DNA in a total reaction volume of 12.5 µl, using for instance Sybr Green RT-qPCR technologies, typically with the following cycle: hold stage of 10 min at 95° C., then 40 cycles of 15 sec at 95° C., 1 min at 63° C. and 1 min at 72° C. Typically, specificity of the qPCR reaction is assessed by analysis of a post-PCR melting curve for example between 60° C. and 95° C.

In a particular embodiment, the method of diagnosing liver fibrosis in an obese subject as defined above further comprises a step a2) of comparing the measured bacterial 16S rDNA concentration, or the 16S rDNA/total DNA ratio, with a threshold value.

Preferably, when the bacterial 16S rDNA concentration is measured at step a2), the threshold value corresponds to a normal concentration of bacterial 16S rDNA. Also preferably, when the 16S rDNA/total DNA ratio is measured at step a2), the threshold value corresponds to a normal ratio of 16S rDNA/total DNA.

As intended herein a "normal concentration" of bacterial 16S rDNA, respectively a "normal ratio" of 16S rDNA/total DNA, means that the concentration of 16S rDNA, respectively the 16S rDNA/total DNA ratio, in the biological sample is within the norm cut-off values for that gene. The norm is dependent on the biological sample type and on the method used for measuring the concentration of 16S rDNA, respectively the 16S rDNA/total DNA ratio, in the biological sample. In particular, the threshold value may be the concentration of bacterial 16S rDNA, respectively the 16S rDNA/total DNA ratio, that gives a negative predictive value and a positive predictive value superior to 80%, preferably superior to 85%, more preferably superior to 90%, even more preferably superior to 95% in the targeted population.

As used herein, the term "targeted population" refers to a population constituted of subjects who share certain biological parameters such as e.g. gender, age group, or certain environmental parameters such as e.g. geographical region.

Preferably, in the methods according to the invention, the threshold value of the 16S rDNA copies/µl of buffy coat is between 460 and 760, still preferably between 550 and 720, most preferably of 675, said threshold value being preferably used when the concentration of bacterial 16S rDNA is measured by real-time PCR, preferably using the universal forward and reverse primers eubac-F (5'-TCCTACGGGAGGCAGCAGT-3', SEQ ID NO: 2) and eubac-R (5'-GGACTACCAGGGTATCTAATCCTGTT-3', SEQ ID NO: 3). Typically, the amplification is performed using 2 µl of DNA in a total reaction volume of 12.5 µl, using for instance Sybr Green RT-qPCR technologies, typically with the following cycle: hold stage of 10 min at 95° C., then 40 cycles of 15 sec at 95° C., 1 min at 63° C. and 1 min at 72° C. Typically, specificity of the qPCR reaction is assessed by analysis of a post-PCR melting curve for example between 60° C. and 95° C.

Preferably, in the methods of the invention, it is further determined whether the measured concentration of bacterial 16S rDNA, or the measured 16S rDNA/total DNA ratio, is increased or decreased compared to the threshold value according to the invention. Still preferably, in the methods of the invention, it is further determined the level of increase or decrease of the measured concentration of bacterial 16S rDNA, or of the measured 16S rDNA/total DNA ratio, compared to the threshold value according to the invention.

As used herein, the expression "level of increase" means the percentage of increase of the measured concentration of bacterial 16S rDNA, or of the measured 16S rDNA/total DNA ratio, compared to the threshold value according to the invention or the number of fold of increase of the measured concentration of bacterial 16S rDNA, or of the measured 16S rDNA/total DNA ratio, compared to the threshold value according to the invention.

Preferably, when the measured concentration or ratio is increased compared to the threshold value, its value is significantly higher than the threshold value.

Also preferably, when the measured concentration or ratio is decreased compared to the threshold value, its value is significantly lower than the threshold value.

The inventors specifically demonstrated that the increase of the 16S rDNA concentration (for instance the number of copies per ml of buffy coat) in the biological sample of a subject compared to the threshold value enabled diagnosing a liver fibrosis with a very high significance, typically with a sensitivity of 91% and a specificity of 73% or a positive predictive value of 88% and negative predictive value of 86%.

Accordingly, in the methods for diagnosing liver fibrosis according to the invention, a concentration or a ratio measured in step a1) which is higher than the threshold value is preferably indicative of the presence of liver fibrosis in the subject.

Also in the methods for diagnosing liver fibrosis according to the invention, a concentration or a ratio measured in step a1) which is lower than the threshold value is preferably indicative of an absence of liver fibrosis in the subject.

Preferably, in the methods for selecting a subject suffering from obesity for liver biopsy according to the invention, the subject is selected to undergo liver biopsy if the concentration or ratio measured in step a1) is higher than the threshold value.

According to another aspect, the invention relates to an in vitro method for selecting a subject suffering from obesity for treatment regimen targeting liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject; and b) based on the result of the measurement in step a1), selecting the subject suffering from obesity to undergo treatment regimen targeting liver fibrosis and/or its complications.

A "treatment regimen targeting liver fibrosis and/or its complications" may for instance be increased surveillance for liver cancer, increased surveillance for oesophageal varices, or drug treatment.

As used herein, "drug treatment" or "drug treatment targeting liver fibrosis and/or its complications" may for instance refer to treatment with a pancreatic lipase inhibitor, a PPARgamma agonist, a leptin analogue, a probiotic or a prebiotic.

In a particular embodiment, the method of diagnosing liver fibrosis in an obese subject as defined above, or the method for selecting a subject suffering from obesity for treatment regimen targeting liver fibrosis and/or its complications as defined above, further comprises a step c) of submitting the subject to a treatment regimen targeting liver fibrosis and/or its complications, if liver fibrosis has been diagnosed in step b).

Methods of Monitoring

The inventors demonstrated that the concentration of bacterial 16S rDNA, or the bacterial 16S rDNA/total DNA ratio, in the biological sample of a subject suffering from fibrosis may be useful in the diagnosis of liver fibrosis. Subjects who have been diagnosed as suffering from liver fibrosis may further benefit from an appropriate monitoring of liver fibrosis or their complications.

Accordingly, another aspect of the present invention is a method for monitoring an obese subject suffering from liver fibrosis and/or complications thereof, said method comprising the steps of:

a1) measuring the concentration of bacterial 16S rDNA, or the ratio of the quantity of bacterial 16S rDNA to the quantity of total DNA, in a biological sample of the subject as defined in the above section "In vitro method for diagnosing liver fibrosis";

b) based on the result of the measurement in step a1), diagnosing liver fibrosis in the subject suffering from obesity as defined in the above section "In vitro method for diagnosing liver fibrosis"; and c) monitoring the subject for complications of liver fibrosis, if liver fibrosis has been diagnosed in step b).

In the context of the invention, the expression "monitoring a subject for complications of liver fibrosis" means submitting said subject to clinical care including for instance ultrasounds for detection of liver cancer, or gastric fibroscopy for detection of varices of the esophagus. Such clinical care is well-known for the skilled person.

Methods of Treatment

According to another aspect, the invention relates to a method for treating a subject suffering from obesity and from liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject;

b) based on the result of the measurement in step a1), diagnosing liver fibrosis in the subject suffering from obesity; and c) submitting the subject selected in step b) to a treatment regimen targeting liver fibrosis and/or its complications.

The invention further pertains to a method for treating a subject suffering from obesity and from liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject;

b) based on the result of the measurement in step a1), selecting the subject suffering from obesity to undergo drug treatment targeting liver fibrosis and/or its complications; and c) administering to the subject selected in step b) a drug treatment targeting liver fibrosis and/or its complications.

In particular, the drug treatment targeting liver fibrosis and/or its complications is as defined in the section "in vitro method for diagnosing liver fibrosis".

The invention also pertains to in vitro method for monitoring the responsiveness of a patient suffering from obesity and from liver fibrosis and/or its complications to a drug treatment targeting liver fibrosis and/or its complications, said method comprising the steps of:

a1) measuring the concentration of bacterial 16S rDNA, or the ratio of the quantity of bacterial 16S rDNA to the quantity of total DNA, in a biological sample of the subject; and b) based on the result of the measurement in step a1), monitoring the responsiveness of the patient to said drug treatment.

The expression "monitoring the responsiveness of a patient to a drug treatment targeting liver fibrosis and/or its complications" may for instance mean adapting the drug treatment. Preferably, "monitoring the responsiveness of a patient to a drug treatment targeting liver fibrosis and/or its complications" means changing the drug used to treat the patient, or increasing or reducing the dose, the administration frequency, or changing the administration route of the drug treatment.

Methods of Screening

The present invention also pertains to method for screening a probiotic, a prebiotic, a chemical compound or a biological compound suitable for preventing and/or treating liver fibrosis, comprising the steps of:

measuring the concentration of bacterial 16S rDNA, or the ratio of the quantity of bacterial 16S rDNA to the quantity of total DNA, in a biological sample of an obese subject suffering from liver fibrosis who has been treated with the candidate probiotic, prebiotic, chemical compound or biological compound; and comparing said concentration, or said ratio, with that of a control obese subject suffering from liver fibrosis who has not been treated with said candidate probiotic, prebiotic, chemical compound or biological compound;

wherein a higher concentration, or a higher ratio, measured in the biological sample of the control subject than in the biological sample of the subject treated with the candidate probiotic, prebiotic, chemical compound or biological compound, indicates that said candidate probiotic, prebiotic, chemical compound or biological compound is suitable for preventing and/or treating liver fibrosis.

As used herein, the term "probiotics" denotes dietary supplements and live microorganisms containing potentially beneficial bacteria or yeasts. According to the currently adopted definition by FAO/WHO, probiotics correspond to live microorganisms which when administered in adequate amounts confer a health benefit on the host. Examples of probiotics according to the invention include bacterial strains of the genera *bifidobacterium, lactobacillus, bacteroides* or of the class fusobacteria.

As used herein, the term "prebiotics" denotes a non-digestible food ingredient that beneficially affects the host by selectively stimulating as a substrate the growth and/or activity of one or a limited number of bacteria in the intestine, in particular in the colon, and thus improves host health.

In the context of the invention, "prebiotics" encompass isolated or purified prebiotics as well as natural prebiotics present in dietary supplements.

In the context of the invention, "probiotics", encompass isolated or purified probiotics as well as natural probiotics present in dietary supplements.

As used herein, the term "chemical or biological compound" encompasses chemically synthetized compounds and compounds of biological origin which have an effect on the growth, metabolism, the survival of bacteria and/or their passage through the intestinal barrier. In particular, chemical or biological compounds according to the invention include molecules which modify the bacterial flora of the digestive tract and/or which modify the migration of bacteria through the digestive tract and/or which modify the permeability of the intestinal epithelial barrier. Examples of chemical or biological compounds of the invention include bactericides, antibiotics, as well as compounds acting on epithelial intercellular tight junctions, microvillies, cell coat, and/or intestinal epithelial cells.

The control subject which has not been treated may be a subject unrelated to the subject receiving the candidate prebiotic, probiotic or chemical or biological compound, or the same subject before treatment with the candidate prebiotic, probiotic or chemical or biological compound.

The invention will be further illustrated by the following examples.

BRIEF DESCRIPTION OF THE SEQUENCES

SEQ ID NO: 1 shows the sequence of the reference *Escherichia coli* 16S rDNA gene.

SEQ ID NO: 2 shows the sequence of the universal rDNA forward primer eubac-F.

SEQ ID NO: 3 shows the sequence of the universal rDNA reverse primer eubac-R.

BRIEF DESCRIPTION OF THE FIGURES

FIG. 1 shows the distribution of the level of 16S bacterial DNA in the blood of 37 patients as measured by a 16S rDNA qPCR assay.

FIG. 2 shows the concentration of blood bacterial 16S rDNA in patients with or without fibrosis, as measured by a 16S rDNA qPCR assay.

FIG. 3 shows the concentration of blood bacterial 16S rDNA in patients with no fibrosis or with fibrosis at various stages, as measured by a 16S rDNA qPCR assay.

EXAMPLE 1

Figure 4:
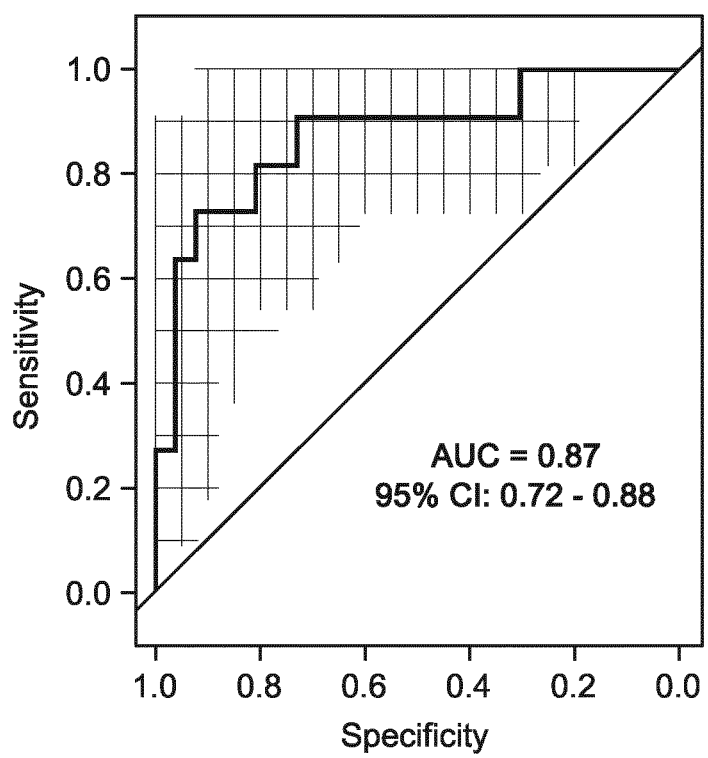
FIG. 4 shows the ROC curve for the diagnosis of liver fibrosis.

Materials and Methods
Population

A cross sectional study was carried out in the Florinash cohort (http://www.florinash.org/). Included patients had severe obesity (BMI>40 or BMI>37.5 plus two metabolic co-morbidities such as Type 2 diabetes, hypertension and dyslipidemia, according to ATPIII) and had been oriented to gastric bypass surgery, once that appropriate lifestyle interventions had failed, to reduce body weight and reduce cardiovascular risk. Exclusion criteria were systemic disease, infection in the previous month, serious chronic illness, >20 g ethanol intake per day. All patients for whom buffy coat fraction samples were available were analysed.

Determination of Blood 16S rDNA Gene Concentration

Total DNA from 100 µl buffy coat fraction were extracted using a Silica-membrane technology kit. Total DNA concentration was determined using the UV spectrometer Nanodrop 2000 (Thermo Scientific). The bacterial DNA (16S rDNA) content was quantified by real-time quantitative PCR (ViiA™ 7 real time PCR System, Life technology) using optical grade 384-well plates. The qPCR reaction was performed using the universal rDNA forward and reverse primers eubac-F (5'-TCCTACGGGAGGCAGCAGT-3', SEQ ID NO: 2) and eubac-R (5'-GGACTACCAGGG-TATCTAATCCTGTT-3', SEQ ID NO: 3). The amplification step was followed by a melting curve step to determine the specificity of the amplification product obtained. The amount of amplified DNA (16S rDNA) was expressed as raw data $2^{-ct}$ or normalized with a plasmid based standard scale of *E. Coli* 16S rDNA. The coefficient of variation (repeatability) of the method (0.24%) was determined using 30 replicate measurements.

Statistical Analysis

The characteristics of the participants who did and did not have fibrosis are shown and non-parametric Mann-Whitney's tests and Fisher's exact tests were conducted on quantitative and categorical variable respectively. Furthermore, the ROC curve for the diagnosis of liver fibrosis is presented.

Results

A bacterial 16S rDNA qPCR assay was performed with blood samples of the 37 patients. This assay revealed, as shown on the distribution of FIG. 1, that two different populations coexist in the cohort: one with a low level and one with a high level of 16S bacterial DNA in the blood which correlate with liver fibrosis status. Analysis of the correlation between fibrosis status of the patients and blood bacterial 16S rDNA concentration showed a very significant increase of blood bacterial 16S rDNA with fibrosis (FIG. 2) which is remarkably correlated to the stage of the disease (FIG. 3). This result demonstrates that liver fibrosis is associated in the cohort to a clear change in the amount of bacterial 16S DNA in the blood which correlates with the severity of the disease.

As shown in FIG. 4, the area under the ROC curve for the diagnosis of liver fibrosis is 0.87.

The characteristics of the population are presented in Table 1. 16S rDNA concentration (copies/µl) was significantly higher in patients with liver fibrosis (Table 1). The distribution of 16S rDNA concentration was shifted towards higher values in patients with liver fibrosis. At a threshold of 675 copies of 16S rDNA/µl of buffy coat, the negative predictive value is 86%, the positive predictive value is 88%, the sensitivity of the test is 55% and the specificity is 96%. At a threshold of 281 copies of 16S rDNA/µl of buffy coat, the negative predictive value is 95%, the positive predictive value is 56%, the sensitivity of the test is 91% and the specificity is 73%.

In conclusion, the results demonstrate that the determination of blood 16S rDNA gene concentration enables diagnosing or ruling out liver fibrosis in obese patients.

TABLE 1

Characteristics of the study population

| Categorical variables | Controls (No fibrosis) Total (n) 26 | | Cases (Fibrosis) 11 | | Cases vs controls |
|---|---|---|---|---|---|
| | n | % | n | % | p (Fisher) |
| Men | 5 | | 2 | | 1.00 |
| Women | 21 | | 9 | | 1.00 |
| Smoking status* | | | | | |
| Never smoked | 12 | 48.0 | 6 | 54.5 | 1.00 |
| Former smoker | 7 | 28.0 | 3 | 27.3 | |
| Current smoker | 6 | 24.0 | 2 | 18.2 | |
| Treated hypertension | 11 | 42.3 | 6 | 54.5 | 0.72 |
| Treated diabetes | 6 | 23.1 | 5 | 45.5 | 0.24 |
| Treated dyslipidemia | 6 | 23.1 | 2 | 18.2 | 1.00 |

TABLE 1-continued

Characteristics of the study population

| Quantitative variables | Mean | SD | Mean | SD | p (Mann-Whitney) |
|---|---|---|---|---|---|
| Age (years) | 46.2 | 8.9 | 48.1 | 9.3 | 0.56 |
| Body mass index (kg/m$^2$) | 44.7 | 6.7 | 41.9 | 6.5 | 0.17 |
| Total cholesterol (mg/dl) | 193.5 | 34.2 | 188.5 | 28.1 | 0.66 |
| HDL cholesterol (mg/dl) | 47.5 | 10.5 | 44.2 | 5.5 | 0.27 |
| GPT (U/l) | 25.2 | 19.29 | 24.36 | 6.454 | 0.17 |
| GGT (U/l) | 20.5 | 9.4 | 23.9 | 7.2 | 0.1 |
| Glucose (mg/dl) | 99.6 | 29.2 | 112.5 | 37.4 | 0.39 |
| C reactive protein (mg/dl)* | 0.73 | 0.44 | 0.78 | 0.75 | 0.57 |
| Hematocrit (%) | 40.5 | 4.6 | 38.6 | 4.0 | 0.33 |
| Leukocyte (10$^3$/μl) | 7.3 | 2.0 | 7.8 | 2.0 | 0.55 |
| Neutrophil (10$^3$/μl) | 4.6 | 1.9 | 4.9 | 1.9 | 0.64 |
| Blood 16S DNA (copies/μl) | 239.3 | 186.4 | 652.6 | 285.4 | 0.0002 |

GPT: Glutamic-Pyruvic Transaminase, GGT: Gamma-glutamyl transpeptidase, HDL: High-density lipoprotein.
*Data is missing for one patient.

The invention claimed is:

1. A method for diagnosing and treating a subject suffering from obesity for a treatment regimen targeting liver fibrosis and/or complications from liver fibrosis, said method comprising
   a1) measuring the concentration of bacterial 16S rDNA, or the ratio of the quantity of bacterial 16S rDNA to the quantity of total DNA in a biological sample of a subject;
   b) diagnosing liver fibrosis in the subject suffering from obesity based on the result of the measurement in a1); and
   c) administering a drug treatment targeting liver fibrosis and/or complications from liver fibrosis to the subject.

2. The method according to claim 1, further comprising a2) comparing the concentration or the ratio measured in a1) with a threshold value.

3. The method according to claim 2, wherein a concentration or a ratio measured in a1) which is higher than the threshold value is indicative of liver fibrosis in the subject.

4. The method according to claim 1, wherein the biological sample is selected from the group consisting of blood, serum and plasma sample.

5. The method according to claim 1, wherein the concentration or the quantities measured in a1) is/are measured by real-time PCR.

6. The method according to claim 1, wherein the subject suffers from non-alcoholic fatty liver disease (NAFL) at the time of sampling.

7. The method according to claim 1, wherein the subject suffers from non-alcoholic steatohepatitis (NASH) at the time of sampling.

8. The method according to claim 1, wherein the subject has a body mass index (BMI) higher than 37.5 kg/m$^2$ and suffers from at least two metabolic co-morbidities selected from the group consisting of type 2 diabetes, hypertension and dyslipidemia.

9. The method according to claim 1, wherein the subject has a body mass index (BMI) higher than 40 kg/m$^2$.

10. The method according to claim 1, wherein the subject did not display infection symptom(s) during the month preceding sampling.

11. A method for selecting a subject suffering from obesity for a treatment regimen targeting liver fibrosis and/or complications from liver fibrosis, said method comprising
    a1) measuring the concentration of bacterial 16S rDNA, or the ratio of the quantity of bacterial 16S rDNA to the quantity of total DNA in a biological sample from a subject suffering from obesity;
    b) diagnosing liver fibrosis in the subject based on the result of the measurement in a1);
    c) selecting the subject to undergo a treatment regimen targeting liver fibrosis and/or complications from liver fibrosis; and
    d) administering a drug treatment targeting liver fibrosis and/or complications from liver fibrosis to the subject.

* * * * *